United States Patent [19]
Bayer

[11] 4,449,936
[45] May 22, 1984

[54] PROCESS FOR THE PREPARATION OF DENTURES

[76] Inventor: Peter Bayer, Nassauerstrasse 6, D-6272 Niedernhausen, Fed. Rep. of Germany

[21] Appl. No.: 415,933

[22] Filed: Sep. 8, 1982

[30] Foreign Application Priority Data

Sep. 8, 1981 [DE] Fed. Rep. of Germany ....... 3135469

[51] Int. Cl.³ .............................................. A61C 9/00
[52] U.S. Cl. .................................................... 433/214
[58] Field of Search ................................. 433/40, 214

[56] References Cited
U.S. PATENT DOCUMENTS 3,413,724 12/1968 Segal ................................. 433/214

FOREIGN PATENT DOCUMENTS 2033822 5/1980 United Kingdom ................. 433/40

*Primary Examiner*—Robert Peshock
*Attorney, Agent, or Firm*—Schwartz, Jeffery, Schwaab, Mack, Blumenthal & Koch

[57] ABSTRACT

Preparation of dental workpieces is facilitated using a rubber elastic mold which is filled with a plastic material and placed in an appropriate location between the working model and counter bite model within an articulator. The working and the counter bite models are moved against each other by closing the articulator, so that a distance remains corresponding to the vertical wall thickness of the mold. The workpiece is formed by the solidifying material within the mold. Following solidification, the mold is removed, the working pattern and the counter bite pattern moved against each other to complete occlusion and the bite inspected. Post-molding operations may then be performed.

8 Claims, 5 Drawing Figures

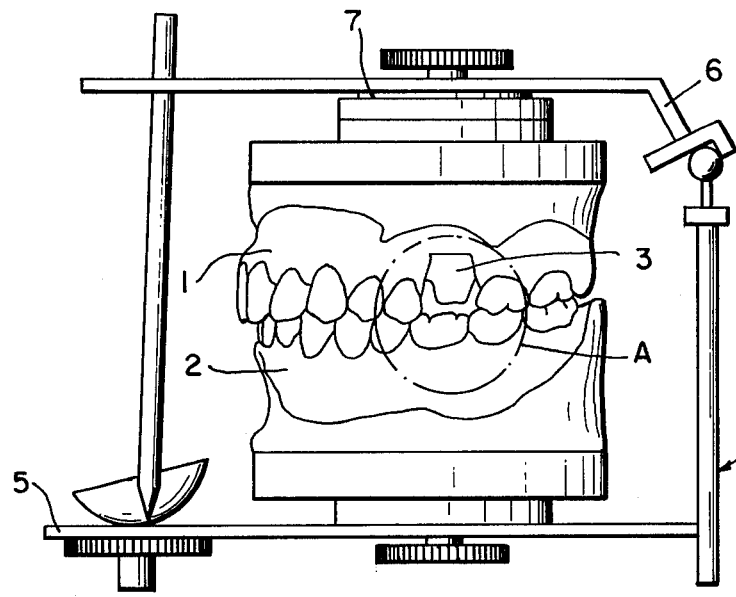
FIG. 1
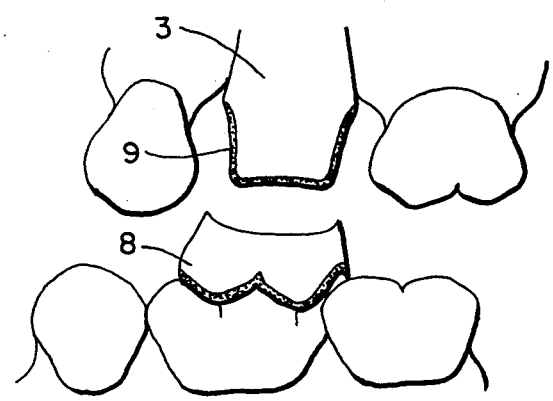
FIG. 3
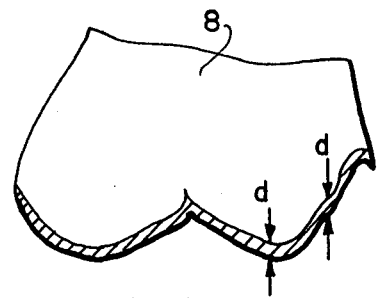
FIG. 2
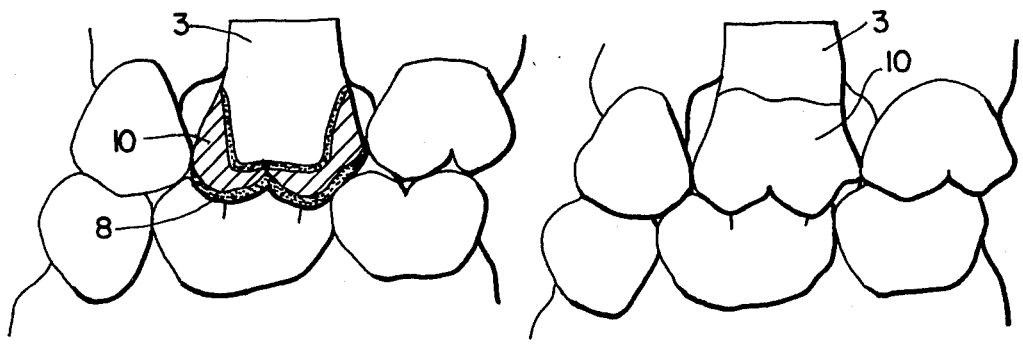
FIG. 4
FIG. 5

PROCESS FOR THE PREPARATION OF DENTURES

BACKGROUND OF THE INVENTION

The present invention concerns the preparation of dental workpieces and more particularly the preparation of workpiece models for denture parts such as crowns or bridges or for workpieces which form directly the denture part, for example, crowns, bridges or facings.

Customarily, in the preparation of dentures, initially a lost wax molding pattern is prepared; it corresponds in its shape to the denture to be made (positive pattern), whereupon with the lost molding pattern, a hollow mold (negative pattern, for example of gypsum) is produced, in which the denture is finally cast.

The molding of such workpieces in an articulator is time consuming and difficult, even if lost patterns made of wax are utilized.

To facilitate the work, semifinished parts in numerous configurations and materials are available. These are in most cases platelets representing the biting surface, which must be backed with supporting material until the workpiece encompasses the stump of the tooth and then shaped in keeping with the articulation movements.

Semifinished parts of this type must therefore be well deformable for further shaping, and adaptation and for this reason usually consist of a wax which is soft and subject to the risk of smearing. Furthermore, semifinished parts made of wax are hardly applicable in the case of minimal space conditions in the area of the chewing surfaces, i.e. when the distance between the tooth stump and the counter biting surface is small. The reason for this is the fact that with a wall thickness of less than 0.5 mm, the semifinished model is no longer stable and may be completely deformed.

If, on the other hand, the semifinished part of a stronger synthetic plastic material is utilized, such as for example described in German Patent DE-OS No. 2 257 724, moldability and adaptation to the individual conditions of the patient are strongly restricted. Frequently the model cannot be molded, but must be machined, i.e. ground.

SUMMARY OF THE INVENTION

It is the object of the present invention to provide a work-saving process requiring lesser effort and less skill for the preparation of dental patterns, which are well adapted to the individual conditions prevailing at the location of the tooth or teeth to be replaced.

To attain the above-mentioned object, in accordance with the invention, a rubber elastic mold for the workpiece to be produced is filled with a plastic material, placed onto the counter bite pattern in the proper location and brought together with the counter bite pattern by means of closing an articulator to the extent that a distance d remains to the occlusion corresponding to the vertical wall thickness of the mold in the area of the occlusion. The mold material is allowed to solidify, whereupon the mold is removed, the working pattern moved against the counter bite pattern until complete occlusion is obtained, the bite inspected and post-molding work performed, to the extent necessary.

In such a process, pattern work is eliminated to a substantial degree, it being restricted essentially to post-molding work.

The above-described distance is assured appropriately by securing, prior to molding, one of the molds (working pattern or counter bite pattern) in the articulator, while inserting a spacer plate of a thickness corresponding to the vertical wall thickness of the mold in the area of the occlusion surface, then effecting the articulation of the patterns and subsequently removing the spacer plate.

If the workpiece consists of a lost pattern, the mold material which forms the workpiece may be a wax or a synthetic plastic which burns without a residue; if, however, the workpiece represents the final denture, a suitable denture material is chosen as the working material; with the additional condition that is must be castable at a temperature low enough not to endanger the mold. Suitable synthetic plastics or ceramic materials may be used.

The mold for the embodiment of the process according to the invention consists of a rubber elastic material and has a constant wall thickness in the area of the occlusion surface, measured in a direction normal to said occlusion surface. The condition that the wall thickness be constant in a direction normal to the occlusion surface signifies that the wall thickness normal to the prevailing surface is not constant, but is at a maximum in the areas parallel to the occlusion surface (i.e. equal to the constant wall thickness in the direction normal to the occlusion surface) and correspondingly less in the steeper areas.

The mold appropriately consists of a silicone rubber or another suitable rubber elastic material.

The invention shall be explained in more detail hereinafter by the description of an example of embodiment and with the aid of the drawings attached hereto. In the drawings:

FIG. 1 shows an overall view of a denture pattern consisting of the working pattern and the counter bite pattern in an articulator;

FIG. 2 shows the mold for the preparation of the workpiece;

FIG. 3 shows the detail A encircled in FIG. 1, with the mold placed onto the counter bite pattern for the production of the workpiece;

FIG. 4 shows the detail A during the hardening of the material;

FIG. 5 shows the detail A after the removal of the mold during the inspection of the bite.

DETAIL DESCRIPTION OF THE PREFERRED EMBODIMENT

The process begins with the taking of a tooth pattern from the teeth of the patient. The part containing a defective area, for example a tooth stump 3 to be capped, is the working model 1, and the other part is the counter bite model 2. The purpose of the work is the preparation of a denture piece filling the gap. The work is performed as usual in an articulator 4, which makes it possible to simulate the chewing movements. In the present case, the counter bite model 2 represents the lower jaw and is fastened in the stationary bottom part 5 of the articulator, while the upper jaw working model is secured to the moving top part 6 of the articulator. The description hereinafter refers to the case where a lost pattern of the cap is to be prepared as a workpiece 10.

Initially, at least one of the models or patterns, in this case the working model 1, is fastened to the top part 6 with the insertion of a spacer plate 7 having a thickness d. The teeth are closed, and the articulator is adjusted to this position. The spacer plate 7 is then removed and the working model 1 fastened without the spacer to the top part 6 so that now there exists a distance d between the entire occlusion surface. The distance d exists between the parallel planes which include the opposing surfaces of the models.

A rubber elastic mold 8, such as that shown in FIG. 2, is now placed, as shown in FIG. 3, onto the counter bite model 2, opposite the tooth gap of the working model 1. The mold may be made from silicone rubber.

The mold 8 is a tub shaped body, the inside bottom or inner surface of which simulates the chewing surface of the tooth replacement to be produced. The mold 8 has a relief configuration of its outer surface corresponding exactly to that of its inner surface. In FIG. 2, the mold is shown in a partial sectioned view in the area of the bottom portion. The sectional surface is shaded, and it may be seen that the upper limiting curve of the sectional surface, representing the cross-sectional cut edge of the inner surface of the mold, corresponding accurately to the lower limiting curve of the sectional surface; this in turn represents the sectional edge of the outer surface of the mold. It is possible to make these curves congruent by visualizing one curve as being displaced parallel to itself in a direction normal (i.e. at right angles) to the occlusion surface. In viewing FIG. 1, this is the vertical direction.

The wall thickness of the mold 8 in the area of the occlusion (chewing) surface is thus constant only in the vertical direction and is designated here as the "vertical wall thickness." It amounts to d as shown in FIG. 2 in two different locations. It may be seen that the real wall thickness, i.e. the thickness measured in the direction normal to the prevailing surface, is equal to d only in the sections parallel to the occlusion surface (horizontal sections), while in the steeper areas the wall thickness is correspondingly lower.

It is obvious that the variation of the wall thickness for the vertical wall sections cannot correspond to a zero wall thickness normal to the surface. In these areas which are remote from the chewing surface, the maintenance of the constant vertical wall thickness condition is no longer important and the mold may terminate sooner.

It is possible to additionally set a cap 9 onto the tooth stump 3 and then fill the mold 8 with liquid wax and close the articulator 4. The working pattern 1 is thereby moved closer to the counter bite pattern 2 to a distance of d remaining because of the removal of the spacer plate 7. This state is shown in FIG. 4; it may be seen therein on the example of the pair of teeth located to the right of the gap, how the bite is not completely closed.

The mold 8 may be filled with a wax material, or other materials suitable for a direct denture material such as a synthetic plastic material or a ceramic material to form a workpiece 10. During the solidification of the material, articulation movements may be effected, so that the material solidifies even initially in a configuration to form a workpiece 10, which takes into account individual conditions. As a result of the exact coincidence of the configuration of the outer surface of the mold with that of the inner surface of the mold in the area of the occlusion surface, the surface of the workpiece 10, following the removal of the mold 8, will have the exact shape assumed by the outer surface of the mold 8 during solidification of the material.

Following the solidification of the material, the mold 8 is removed and the workpiece 10 exposed. The spacer plate 7 is then reinserted and the articulator closed. This state, wherein complete occlusion of the denture is present, is shown in FIG. 5. hand finishing may now be performed as needed.

In practicing the invention, the mold 8 is previously made to conform to the shape of standard or average teeth. A desired tooth shape may be selected by the dental technician. The mold may be made, for example, using male and female gypsum blocks. Standard teeth models are made to protrude from the male block, and the female block is formed by pouring gypsum onto the male block and holding the two blocks together so that the recessed portions of the female block correspond exactly to the "negative" of the surface form of the male block. Pins secured to one of the blocks and registering in holes in the other block may be used to insure registration of the two blocks. Next, the mold 8 is formed by pouring a suitable silicone material onto the recessed patterns of the female block. A spacer element of thickness d is now placed on the female block adjacent the edges thereof (so as not to interfere with the recessed pattern area), and the male block is placed in registration over the female block so that it is supported a distance d from the female block. The silicone material is allowed to harden after polymerization, the blocks are taken apart and the silicone material mold 8 with ribber-like properties is produced.

I claim:

1. A process for preparing a workpiece for use as denture parts or denture models comprising the steps of:
    (a) arranging a working model to which the workpiece is to be secured and a counter bite model in an articulator;
    (b) arranging a mold between opposing surfaces of said models in the area between said working model and counter bite model;
    (c) filling said mold with a hardenable material;
    (d) bringing together said working model and counter bite model in said articulator so that parallel planes which include the opposing surfaces of said models are spaced apart by a distance d, said distance corresponding to the wall thickness of said mold in the direction normal to said planes;
    (e) allowing said hardenable material to solidify; and
    (f) removing said mold, whereby a hardened workpiece is formed.

2. A process as recited in claim 1 further including the step of performing post-molding operations on said workpiece.

3. A process as recited in claim 1 wherein step (d) is effected by means of a spacer plate having a thickness d inserted between a support member of said articulator and one of said working models and said counter bite models.

4. A process as recited in claim 1 wherein wax is said material and said workpiece is a wax denture model.

5. A process as recited in claim 1 wherein synthetic plastic is said material and said workpiece is a synthetic plastic model, said synthetic plastic burnable without residue.

6. A process as recited in claim 1 wherein ceramic is said material and said workpiece is used directly as said denture part.

7. A mold for use in the process of claim 1 comprising a rubber elastic material having a wall thickness d measured normal to the direction of said planes.

8. A mold as recited in claim 7 wherein said mold comprises silicone rubber.

* * * * *